United States Patent [19]
Kallassy

[11] Patent Number: 5,090,404
[45] Date of Patent: Feb. 25, 1992

[54] UNIVERSAL ANKLE SUPPORT

[76] Inventor: Charles Kallassy, 9655 Lakemont Dr., Dallas, Tex. 75220

[21] Appl. No.: 477,058

[22] Filed: Feb. 7, 1990

[51] Int. Cl.⁵ .............................................. A61F 5/00
[52] U.S. Cl. ...................................... 602/65; 602/66; 602/23
[58] Field of Search ............... 128/80 R, 80 C, 80 H, 128/80 J, 80 D, 83, 83.5, 87 R, 165, 166; 2/22; 36/89, 91

[56] References Cited

U.S. PATENT DOCUMENTS

| | | | |
|---|---|---|---|
| 3,383,708 | 5/1968 | Pappas | 2/22 |
| 3,506,000 | 4/1970 | Baker | 128/80 R |
| 4,729,370 | 3/1988 | Kallassy | 128/166 |
| 4,878,504 | 11/1989 | Nelson | 128/80 H |

Primary Examiner—Richard J. Apley
Assistant Examiner—Lynne Reichard

[57] ABSTRACT

An ankle support is disclosed which includes an underliner extending about the wearer's leg at a point above the ankle joint and forming a main body for the ankle support. An upper strap extends about the underliner at a point above the ankle joint and is adjustable in tension. An upright strap is secured to the underliner and this upright strap extends downwardly on the medial side of the wearer's leg, under his arch and upwardly along the lateral side of the wearer's leg, where it is secured to the upper strap. A diagonal strap is secured to the upright strap and the underliner on the medial side of the wearer's leg and extends upwardly and forwardly across the wearer's ankle, and around the lateral side of the wearer's leg to be joined to the upper strap. This construction not only supports the ankle joint against inversion sprains, but provides support for the arch and the plantar fascia.

18 Claims, 2 Drawing Sheets

UNIVERSAL ANKLE SUPPORT

FIELD OF THE INVENTION

The present invention relates generally to ankle braces and, more particularly, concerns an ankle support which is fully adjustable to a wide range of sizes, for providing firm support for the joint and ligaments of the ankle, without affecting their normal function.

BACKGROUND OF THE INVENTION

Traditionally, adhesive tape, or the like, has been applied to an injured or weakened ankle, in order to support the joint and ligaments thereof during physical activity. Although taping could lend significant support to the ankle, a substantial amount of time and effort is required in order to apply the tape properly, and the perspiration and rigors of physical activity can result in the loss of a significant proportion of the support after less than twenty minutes of use. Furthermore, after tape has been applied to the ankle of an athlete and he has had an opportunity to warm-up for several minutes, he may experience cramping, pinching or some other form of discomfort in one or more areas of the foot. To relieve this discomfort, little cuts are made in the tape in the areas of discomfort, in an effort to loosen the tape locally. However, each time such a cut is made, some of the strength of the tape is lost, and an early loss of the effectiveness of the entire structure becomes more likely. In an effort to overcome some of the shortcomings of taping, use has been made of ankle braces. A typical prior art brace takes the form of a sheathe or stocking which is worn on the foot and lower leg. Some braces have made provision for selective tightening and adjustability, for example by means of laces. One shortcoming of such ankle braces is that they do not provide effective support to the lateral ligaments in the ankle and, to get any support, they must be secured so tightly that pinching and interruption of dorsal flexion occur. Securing the brace as tightly as needed for any meaningful support therefore would interfere with normal movement.

Another type of known ankle brace is a lace-up model with an elastic strap that fits over and around the ankle to provide elastic support for the ankle. The problem with elastic straps and the like is that they provide compression but very little support.

Other braces in use today, have little pockets that receive metal stays. They are used primarily for acute injuries, because they limit normal motions of the foot to an extreme degree and, if worn on a continued basis, can produce atrophy of the musculature in the region.

In accordance with the disclosure of my own U.S. Pat. No. 4,729,370, an ankle support is provided with an underliner having multi-directional stretch which fits over the wearer's foot in the manner of a sock and extends to a point above the ankle. A non-stretch lateral strap is secured to the underliner at a point below the ankle joint and extends upwardly to the top of the underliner, where it is inelastically secured, with provision being made for adjustment of its tension. A non-stretch medial strap is inelastically connected to the lateral strap therebelow. The medial strap extends underneath the foot and up the opposite side thereof, and it is inelastically secured to the leg near the top of the underliner, with provision being made for adjustment of its tension. The medial strap thereby supports the wearer's arch and, in combination with the lateral strap, supports the ligaments of the ankle joint and provides a "heel lock", to limit and balance the lateral movement of the ankle joint.

Although the ankle brace of my patent overcame the shortcomings of known ankle braces, and it provided more convenient and rapid adjustment than other ankle supports known at the time, it still had a number of disadvantages. First of all, its construction made it impossible to make the ankle brace in a single size that would fit all wearers. Furthermore, the requirement to adjust a multitude of straps made application of the device by an average user difficult, and even for an experienced user the process was somewhat cumbersome and slow. In addition, the sock-like construction of the device complicated manufacture. Also, although the device was far more unobtrusive than other devices known at the time, it occupied substantially more space than a heavy sock and interfered with the comfort of shoes in which it was worn.

Broadly, it is an object of the present invention to overcome the disadvantages associated with ankle taping and prior ankle supports. It is a specific object to provide an ankle support which may be quickly and easily applied to and adjusted upon the wearer's leg, while offering a high degree of firm, inelastic support for the ankle joint, and not interfering with normal movement and use of the joint.

It is another object of the present invention to provide an ankle brace with a high degree of adjustability, in order to accommodate a wide range of sizes and shapes of legs and feet with a single device.

It is further object of the present invention to provide an ankle support which, when applied, does not change the shoe size of the wearer's foot and may be worn comfortably inside the wearer's normal shoe.

It is also an object of the present invention to provide and ankle support which is convenient, efficient and effective in use, yet relatively simple and inexpensive in construction and capable of efficient manufacture.

In accordance with the present invention, an ankle support which includes an underliner extending about the wearer's leg at a point above the ankle joint and forming a main body for the ankle support. An upper strap extends about the underliner at a point above the ankle joint and is adjustable in tension. An upright strap is secured to the underliner and this upright strap extends downwardly on the medial side of the wearer's leg, under his arch and upwardly along the lateral side of the wearer's leg, where it is secured to the upper strap. A diagonal strap is secured to the upright strap and the underliner on the medial side of the wearer's leg and extends upwardly and forwardly across the wearer's ankle, and around the lateral side of the wearer's leg to be joined to the upper strap. This construction not only supports the ankle joint against inversion sprains, but provides support for the arch and the plantar fascia.

BRIEF DESCRIPTION OF THE DRAWING

The foregoing brief description, as well as further objects, features, and advantages of the present invention will be understood more completely from the following detailed description of a presently preferred, but nonetheless illustrative, embodiment of the present invention, with reference being had to the accompanying drawings in which.

DETAILED DESCRIPTION

Figure 3:
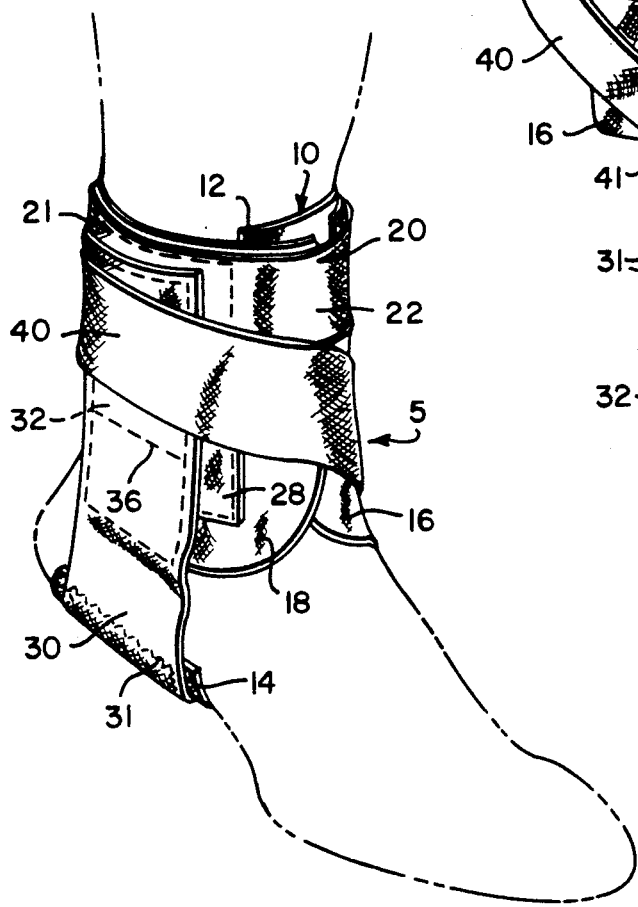
FIG. 3 is a perspective view showing the ankle support after application to the wearer's leg.
Figure 4:
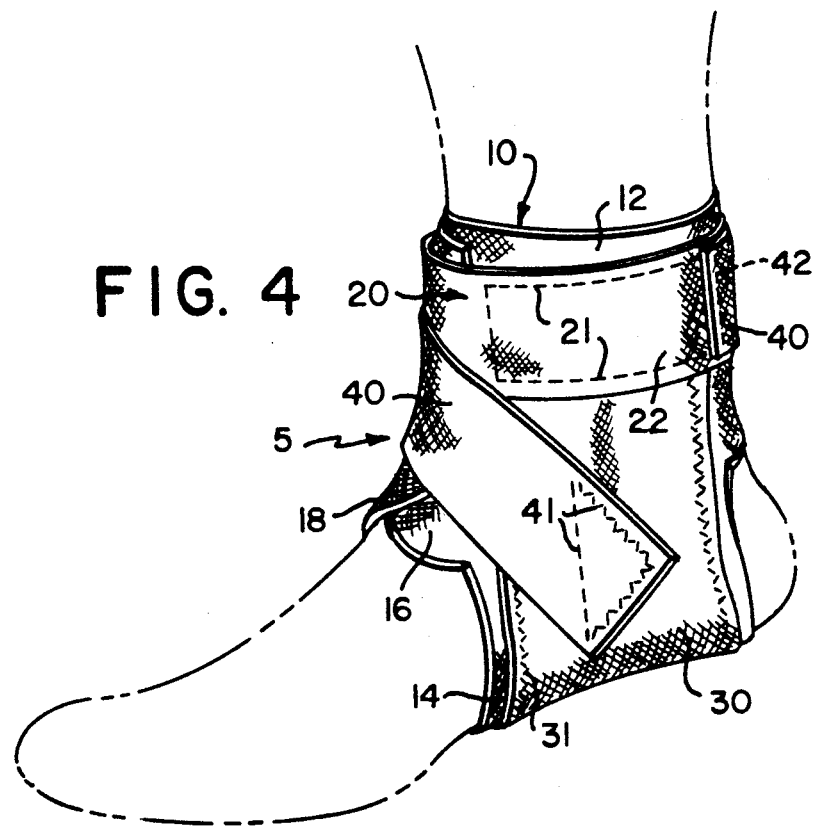
FIG. 4 is a right side with respect to FIG. 3.

Turning now to the details of the drawing, FIGS. 1-5 illustrate an ankle support 5 embodying the present invention, and FIGS. 3 and 4 illustrate the support 5 applied to the right leg of a wearer. The support 5 would be provided in an opposite version (a mirror image of the version illustrated) for use on the left leg, but a single size would fit all normal leg sizes (e.g., small, medium and large). As will be explained more fully below, after application, the support 5 remains in the position shown and will readily fit inside the wearer's shoes, occupying no more space than an average athletic sock. Adjustments to the device can be made quickly and easily, without removing the shoe.

Figure 1:
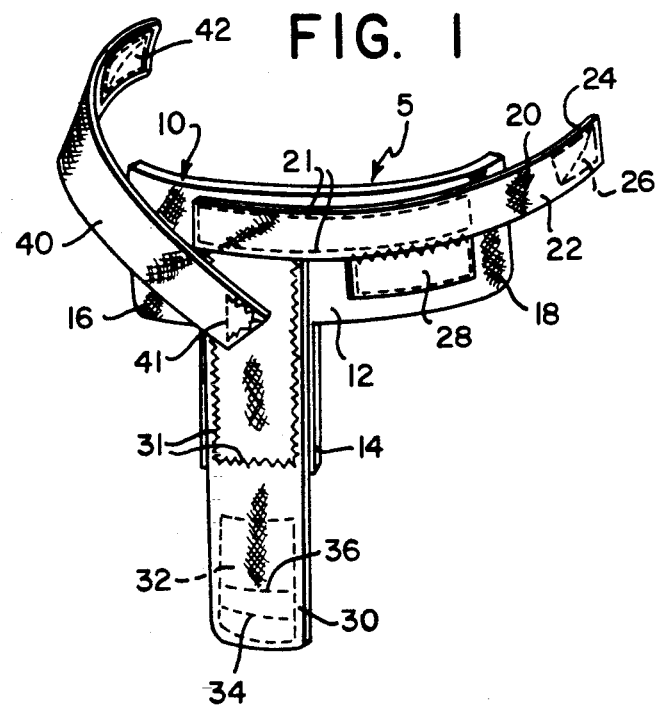
FIG. 1 is a perspective view showing an ankle support in accordance with the present invention in its open position, prior to being applied to the leg of a wearer.
Figure 2:
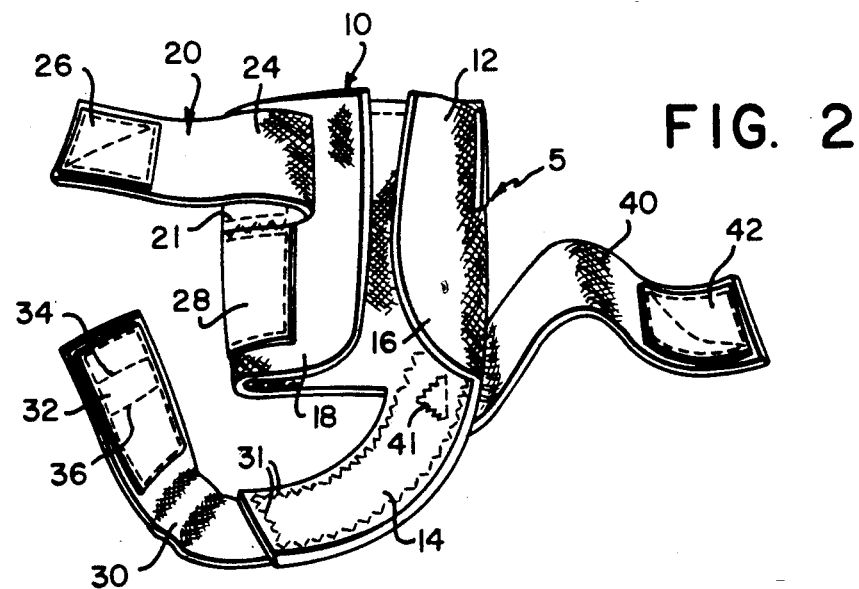
FIG. 2 is a perspective view showing the ankle support of FIG. 1 with the various components being manipulated towards the positions they assume when the support is applied to the wearer's leg.

The construction of support 5 is best seen in FIGS. 1 and 2. As will be appreciated from FIG. 1, the entire device may be manufactured as a flat, planar structure. This makes manufacture far simpler than prior devices, including that of my above-described patent, which were manufactured in the form of a sock or a partially closed structure. Those skilled in the art will also appreciate that this flat structure may be applied more easily and quickly to any size leg.

The main body of ankle support 5 is an underliner 10, which is preferably made of a rubberized material, such as neoprene foam. Such a rubberized material is used, because it will not slip on the wearer's leg because of its high friction surface, yet it is soft and will not retain bacteria, fungi or other organisms that could propagate. Preferably, a fabric layer, such as nylon is laminated over the outer surface of the neoprene. The principal function of the underliner is to carry the remaining components of the support 5 and to pad the wearers leg against the chafing and abrading effect of the strapping and bracing components.

Underliner 10 is generally T-shaped. The top or cross-piece 12 of the T-shape is about thirteen inches long and about four an one-half inches high. The upright leg 14 of the T-shape is about four inches across and about four and one-half inches high. It is offset towards the left (in FIG. 1) with respect to the vertical center line of cross-piece 12. In the preferred embodiment, vertical center line of leg 14 is offset about two inches with respect to the vertical center line of cross-piece 12. The lower corners of cross-piece 12 are rounded to form fan-shaped corners 16 and 18, by means of which a better fit is achieved for a wide range of leg sizes, as will become more apparent below.

An upper strap 20 made of a light weight, nonstretchable web material is attached, as by sewing (stitching shown at 21), so as to extend along the upper edge of cross-piece 12. Strap 20 is preferably about sixteen inches long and about two inches high. In the preferred embodiment, strap 20 is attached to cross-piece 12 so that its left edge is about two inches to the right (in FIG. 1) of the left edge of cross-piece 12, and the right edge of strap 20, which defines a free end, will then extend well beyond the right edge of cross-piece 12. The front surface 22 of strap 20 is preferably covered with the pile portion of a hook-and-pile fastener. In addition, a portion of the end of strap 20 is covered on its undersurface 24 with a strip 26 of hook-type material. In the preferred embodiment strip 26 extends, from the right edge of strap 20, back about three and one-half inches. Strap 20 also includes a depending portion 28, which is about four inches long and two inches high. Portion 28 is set back about one and one-half inches from the right edge of cross-piece 12. Portion 28 is also covered with a pile-type material.

An upright strap 30, made of a non-stretch, light weight webbing material is secured to underliner 10 and strap 20, as by sewing (stitching shown at 31), so as to extend along leg portion 14. In the preferred embodiment, strap 30 is about three and one-half inches across and about fourteen inches high. On its undersurface, strap 30 is provided with a section 32 of hook-type material which extends upwardly from its lower edge for about four inches. Section 32 is preferably attached to strap 30 by sewing, and it preferably includes additional lines of stitching 34, 36 at an inch and two inches, respectively, above the lower edge of strap 30. These additional rows of stitching allow strap 30 to be cut, for purposes of adjustment, without leaving an open stitch. The importance of being able to cut strap 30 in this manner will become more apparent below.

A diagonal strap 40, made of a non-stretchable, light webbing material, is attached, as by sewing (stitching shown at 41), over upright strap 30 and underliner 10. Strap 40 is about thirteen inches long and about two inches wide in the preferred embodiment, and it is attached at an angle of about forty degrees with respect to strap 30. Stitching 41 includes an upright portion of stitching, preferably, generally perpendicular to cross-piece 12, which is positioned about three and three-quarter inches below the top edge of underliner 10 and one and one-half inches from the right edge of leg portion 14 of underliner 10, in the preferred embodiment. On its undersurface, Strap 40 includes a portion 42 of hook-type material which extends back for about three inches from the upper end of strap 40.

FIG. 2 illustrates the manipulation of the various components of ankle support 5 in applying it to the wearer's leg. The support is seen from the front, as it would be applied to the leg. Initially, cross-piece 12 is wrapped around the wearer's ankle, above the ankle joint, so that corner 18 overlaps corner 16 and both corners rest against the top of the wearer's instep (see FIG. 3). With cross-piece 12 so positioned, strap 20 is wrapped circumferentially about the leg above the ankle joint so as to retain cross-piece 12 firmly in position. Eventually, portion 26 of strap 20 comes into contact with surface 22 thereof, so that the hook and pile components come into engagement and retain cross-piece 12 in position. In addition, the snug pressure of strap 20 against the distal ends of the tibia and fibula gives support to the anterior tibiofibular ligament, which aids in resisting and preventing lateral ligament sprains to the ankle.

With the cross-piece 20 held in position, the upright strap 30 is pulled firmly under the patient's foot and up along the lateral margin of the ankle, at which time component 32 is pressed against the surface 22 and/or surface of element 28, causing upright strap 30 to remain in contact therewith.

Figure 5:
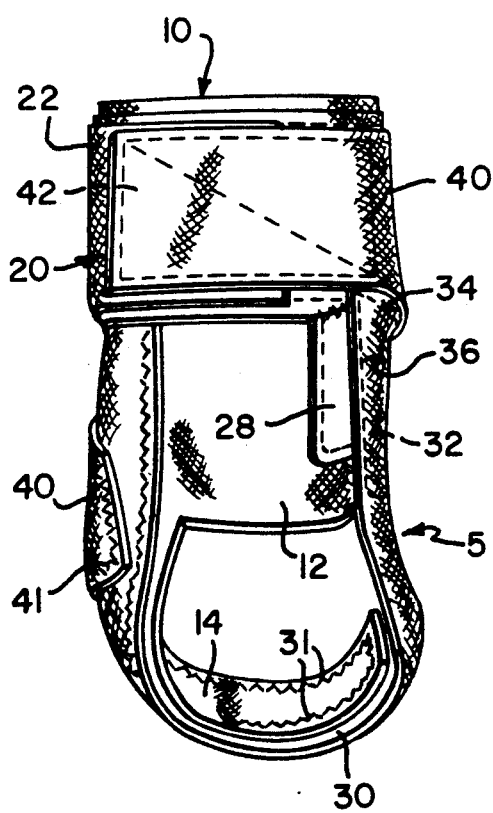
FIG. 5 is a rear view with respect to FIG. 3, with the leg eliminated to show interior details of the ankle support as worn.

The application of ankle support 5 is then completed by pulling diagonal strap 40 across the front of the wearer's ankle (see FIGS. 3 and 4), over strap 20 (see FIG. 3), and behind the wearer's leg, bringing component 42 of strap 40 into contact with surface 22 of strap 20 at the rear of the wearer's leg (see FIG. 5). The strap 40 is then retained in contact with strap 20.

FIGS. 3 and 4 illustrate the ankle support 5 as applied to a wearer's leg. It will be appreciated that the fan-shaped edges 16 and 18 of the cross-piece 10 facilitate rapid application of the cross-piece to the leg and convenient adjustment to fit about the leg. In addition, leg 14 of underliner 10 is interposed between the wearer's arch and upright strap 30. In this position, it serves to protect and pad the arch against chafing and abrasion by strap 30. At the same time, strap 30 provides support to the lateral ligaments of the ankle by resisting inversion sprains to the joint. It also provides support directly to the transverse and longitudinal arches of the foot and resists excess pronation of the foot. The support which strap 30 provides to the plantar fascia on the bottom of the foot can be effective treatment for plantar fasciitis.

If the wearer has a small leg, strap 30 may project above strap 20 and could become uncomfortable or cumbersome. The lines of stitching 34, 36 permit the strap to be cut back by one inch at a time so as to customize the fit, without stitches unraveling.

With the ankle support 5 in its worn position, diagonal strap 40 presses the end of strap 30 against the strap 20, retaining it in position and assuring that it will not become undone accidentally during physical activity. In addition, strap 40 prevents the entire support 5 from migrating backwards as the foot is plantarflexed, when the ankle is subjected to the forces of inversion, or with repeated flexon and extension of the foot. This action is assisted by the rubberized, non-slip inside surface of upright leg 14, which is in contact with the wearer's arch. Owing to the upright portion of stitching 41, the strap 40 also asserts an upward pull on upright strap 30, which assists in supporting the plantar fascia and the traverse arch of the foot. From FIG. 5, it will also be appreciated that the strap 40 assists strap 20 in holding together the distal ends of the tibia and fibula and provides support to the anterior tibiofibular ligament, which aids in resisting and preventing lateral ligament sprains.

From FIGS. 3 and 4, it will also be appreciated that the bulky portion of the ankle support is above the ankle joint and only the stirrup structure defined by strap 30 is below the ankle joint. This construction provides maximum support, while very little of the bulk of the ankle support is within the wearer's shoe. In addition, the stirrup nature of strap 30 permits the heel of the leg to extend rearwardly, out of the ankle support, which allows for maximum comfort and fit.

Although a preferred form of the invention has been disclosed for illustrative purposes, those skilled in the art will appreciate that many additions, modifications, and substitutions are possible without the departing from the scope and spirit of the invention as defined in the accompanying claims.

What is claimed is:

1. An ankle support for a wearer's leg, comprising:
   an underliner defining a main body for said support, said underliner having generally a T-shape defined by a cross-piece having a forward and rear edge and an upright leg generally perpendicular to said cross-piece and positioned to be closer to said front edge than said rear edge;
   a non-stretch upper strap of length sufficient to extend about the wearer's ankle secured on the exterior surface of the underliner so as to extend from a point intermediate said front and rear edges to a point beyond said rear edge to a free end of said upper strap;
   first securing means for inelastically securing said upper strap about a wearer's leg so that the tension of said strap may be selectively adjusted;
   a non-stretch upright strap secured to the exterior surface of said underliner so as to be secured to a portion of said upper strap, to extend along the leg portion of said underliner, and to extend beyond said leg portion thereof to terminate in a free end;
   second securing means for securing the free end of said upright strap with said upper strap so that the free end of said upright strap maybe selectively positioned relative to said upper strap;
   a diagonal strap secured to said upright strap and said underliner so as to be oriented diagonally relative to said upright strap and extending upwardly towards the forward edge of said cross-piece to a free end of said diagonal strap; and
   third securing means for securing the free end of said diagonal strap to selected position on said upper strap.

2. An ankle support in accordance with claim 1, wherein said first securing means comprises a first component of a hook-and-pile closure material formed on a first surface of said upper strap and the other component of a hook-and-pile closure material formed on the opposite surface of said upper strap at the free end thereof.

3. A ankle support in accordance to claim 2, wherein said second securing means comprises a portion made up of said other component of a hook-and-pile closure material formed at the free end of said upright strap in a position to cooperate with the first hook-and-pile closure material surface on said upper strap.

4. An ankle support in accordance with claim 3, wherein said third securing means comprises a portion made up of said other component of a hook-and-pile closure material formed at the free end of said diagonal strap in a position to cooperate with the first hook-and-pile closure material surface on said upper strap.

5. An ankle support in accordance with claim 2, wherein said third securing means comprises a portion made up of said other component of a hook-and-pile closure material formed at the free end of said diagonal strap in a position to cooperate with the first hook-and-pile closure material surface on said upper strap.

6. An ankle support in accordance with claim 2, further comprising a portion said first of type of said hook-and-pile material secured to said underliner so as to depend from said upper strap.

7. A ankle support in accordance to claim 6, wherein said second securing means comprises a portion made up of said other component of a hook-and-pile closure material formed at the free end of said upright strap in a position to cooperate with the first hook-and-pile closure material surface on said upper strap.

8. An ankle support in accordance with claim 7, wherein said third securing means comprises a portion made up of said other component of a hook-and-pile closure material formed at the free end of said diagonal strap in a position to cooperate with the first hook-and-pile closure material surface on said upper strap.

9. An ankle support in accordance with claim 1, further comprising fan-shaped lower corners formed at the forward end rear edges of said cross-piece.

10. An ankle support as in claim 1 wherein said diagonal strap is secured to said underliner by means of stitching which includes a row of stitching generally perpendicular to said cross-piece.

11. An ankle support for a wearer's leg comprising:
an underliner defining a main body for said support and being formed to fit about the wearer's leg at a point above his ankle;
an non-stretch upper strap secured to the exterior surface of said underliner at a point above the ankle joint so as to extend about the wearer's leg;
first securing means for selectively adjusting the tension of said upper strap about the wearer's leg;
a non-stretch upright strap secured to the exterior surface of said underliner and to said upper strap so as to extend downwardly therefrom, under the user's arch and upwardly along the other side of the user's leg to terminate in a free end;
second securing means for securing the free end of said upright strap to said upper strap on the other side of the user's leg;
a diagonal strap secured to said upright strap and said underliner proximate to the point of securement of said upper strap and said upright strap to said underliner, said diagonal strap extending upwardly and forwardly across the front of the user's leg, along said other side of said leg and rearwardly to terminate in a free end; and
third securing means for securing the free end of said diagonal strap to said upper strap.

12. An ankle support in accordance with claim 11, wherein said first securing means comprises a first component of a hook-and-pile closure material formed on a first surface of said upper strap and the other component of a hook-and-pile closure material formed on the opposite surface of said upper strap at the free end thereof.

13. A ankle support in accordance to claim 12, wherein said second securing means comprises a portion made up of said other component of a hook-and-pile closure material formed at the free end of said upright strap in a position to cooperate with the first hook-and-pile closure material surface on said upper strap.

14. An ankle support in accordance with claim 13, wherein said third securing means comprises a portion made up of said other component of a hook-and-pile closure material formed at the free end of said diagonal strap in a position to cooperate with the first hook-and-pile closure material surface on said upper strap.

15. An ankle support in accordance with claim 12, further comprising a portion of said first of type of said hook-and-pile material secured to said underliner so as to depend from said upper strap.

16. An ankle support in accordance with claim 10, further comprising a portion of said underliner extending behind said upright strap so as to be interposed therebetween and the arch of the wearer's foot.

17. An ankle support in accordance with claim 11, further comprising fan-shaped lower corners formed at the forward end rear edges of said cross-piece.

18. An ankle support as in claim 1 wherein said diagonal strap is secured to said underliner by means of stitching which includes a row of stitching generally perpendicular to said cross-piece.

* * * * *